United States Patent [19]
Kilbey

[11] Patent Number: 5,290,218
[45] Date of Patent: Mar. 1, 1994

[54] SHOULDER RESTRAINT

[75] Inventor: Bryan Kilbey, DeFuniak Springs, Fla.

[73] Assignee: Professional Products, Inc., DeFuniak Springs, Fla.

[21] Appl. No.: 978,993

[22] Filed: Nov. 19, 1992

[51] Int. Cl.⁵ .................. A61F 5/00; A61F 5/37; A61B 19/00
[52] U.S. Cl. .................. 602/4; 602/14; 128/869; 128/875
[58] Field of Search .............. 128/869, 870, 872, 873, 128/874, 875, 876; 602/4, 5, 14, 19, 62, 60, 61

[56] References Cited

U.S. PATENT DOCUMENTS

| | | | |
|---|---|---|---|
| 3,463,147 | 8/1969 | Stubbs | 602/62 |
| 3,548,819 | 12/1970 | Davis | 602/14 |
| 3,561,435 | 2/1971 | Nicholson | 602/14 |
| 3,628,537 | 12/1971 | Berndt | 602/14 |
| 3,906,944 | 9/1975 | Christen | 128/869 |
| 4,423,720 | 1/1984 | Meier | 602/62 |
| 4,484,572 | 11/1984 | Dobson | 128/875 |
| 4,598,703 | 7/1986 | Lindemann | 602/4 |
| 4,986,266 | 1/1991 | Lindemann | 602/4 |

Primary Examiner—Michael A. Brown
Attorney, Agent, or Firm—George A. Bode

[57] ABSTRACT

This invention pertains to a shoulder restraint having a series of pockets therein that is wrapped around the user's shoulder to apply hot or cold packs to the affected area. This restraint comprises a main body portion and two extensions, one short and one long, extending from the same side of the main body portion. Each extension is secured to the main body portion (after being wrapped around the user's body part) by closure means that comprise the "hook" portion of a typical hook and loop closure system. The pockets are closed in a similar manner to retain the hot or cold packs therein, and to provide a means to remove and/or replace these packs without the need to remove the restraint.

9 Claims, 2 Drawing Sheets 5,290,218

SHOULDER RESTRAINT

BACKGROUND OF THE INVENTION

1. Field of the Invention

This invention pertains to medical devices in general, and more particularly to a flexible wrap for restraining a shoulder, or another anatomical part of a user, in a relatively stable position while also providing a means for applying either a heat pack or a cold pack to that region of the body.

2. General Background

The medical field contains numerous examples of flexible restraints for body parts ranging from a simple strip bandages to more complicated devices designed for a specific body part. As can be imagined, the more complicated the design, the less utilitarian it becomes, in some cases requiring a separate device for the right and the left (or the front and the back) body part. Another drawback to the more specific designs of restraints is the fact that they must come in a variety of sizes to accommodate men, women and children and their respective ectomorphic, mesomorphic and endomorphic body sizes and/or shapes.

In the past, shoulder restraints have ranged from multiple wraps of gauze to a full upper body cast or plaster, depending upon the degree of movement permitted. Regardless of the type specified, each of them required a considerable amount of time to secure or install in place, and they oftentimes required the assistance of another person for proper fit. This becomes a burden when the wrap needs to be frequently removed for inspection, change of dressing, or application of medicine purposes. These wraps also fail to provide a means for securing a heating source or a chilling source against the affected area, much less enable these sources to be replaced in a timely and efficient manner.

It is thus an object of this invention to provide a shoulder restraint that can be quickly installed, adjusted and removed as needed. Another object of this invention is to enable this installation/removal to be accomplished by user, without the need for assistance. Still another object of this invention is to provide a means for securing a heat source or a chilling source against the affected area without the need to remove the wrap when the source must be removed and/or recharged. A further object of this invention is to provide a shoulder restraint that can be used on either shoulder and on both men and women despite their body size or category. Yet another object is to enable the user to quickly adjust the amount or restraint provided by the wrap to accommodate a variety of needs or requirements. These and other objects will become obvious upon further inspection.

SUMMARY OF THE PRESENT INVENTION

The preferred embodiment of the apparatus of the present invention solves the aforementioned problems in a straightforward and simple manner. What is provided is a shoulder restraint comprising of a generally planar main body portion having at least one pocket therein. This pocket is sized and configured to accept either a hot or a cold pack therein. Extending from the same side of this main body portion are two extensions, one short and one long. Both extensions are of the same construction and generally the same thickness as the main body portion. Detachable closure means are provided to secure these extensions around the user's body and to the main body portion and also to secure the pockets closed.

BRIEF DESCRIPTION OF THE DRAWING

For a further understanding of the nature and objects of the present invention, reference should be had to the following description taken in conjunction with the accompanying drawings in which like parts are given like reference numerals and, wherein.

DETAILED DESCRIPTION OF THE PREFERRED EMBODIMENT

Figure 1:
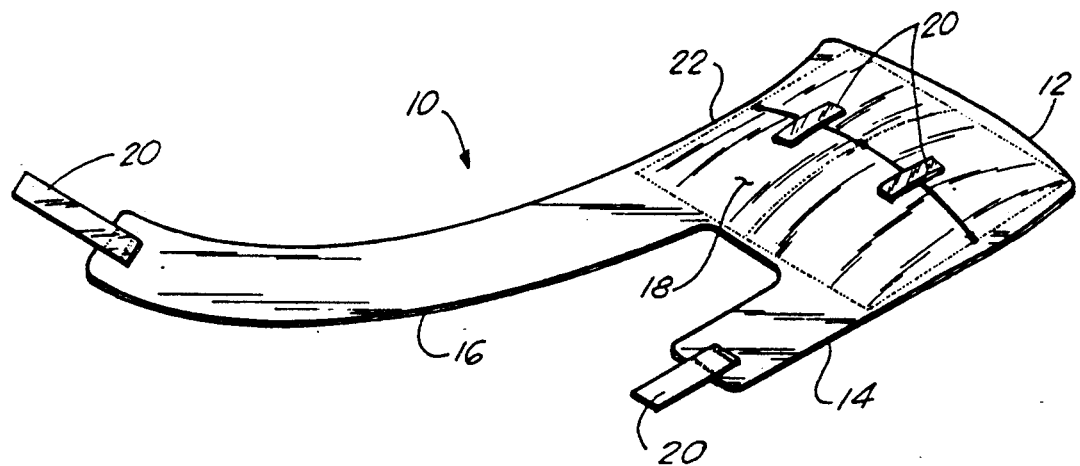
FIG. 1 is a top perspective view of the preferred embodiment of the apparatus of the present invention.

Referring now to the drawings, and in particular FIG. 1, the apparatus of the present invention is designated generally by the numeral 10. Apparatus 10 is generally comprised of main body portion 12, short extension 14 and long extension 16. More extensions may be incorporated as needed, but generally two are sufficient. As shown, shoulder restraint 10 is generally flat or planar in configuration with main body portion 12 having a plurality of pockets 18 therein, thus being slightly thicker in construction. Shoulder restraint 10 is also preferably constructed of a thin foam material thereby providing some padding and comfort to the user. Additionally, the exterior surface of this foam material preferably operates as the "loop" portion of a typical "VELCROR" hook and loop closure system so that the ends of extensions 14 and 16 may be secured anywhere to main portion 12 or even back onto themselves.

As shown, short extension 14 and long extension 16 are both secured along the same side of main body portion 12. Short extension 14 may extend linearly from main body portion 12 or it may be curved slightly. In contrast, it is preferable for long extension 16 to be curved as shown for better fit to the user. During operation, short extension 14 is to be wrapped around the user's arm region while longer extension 16 is to be wrapped around the user's torso. Both such extensions are thereafter secured to main body portion 10 via hook closure device 20 of a typical hook and loop closure system. Hook closure device 20 is completely removable from shoulder restraint 10 for maximum utilization and so that restraint 10 may be fitted onto either shoulder of the user.

At the base of long extension 16 is neck notch 22 that is configured to accommodate the wrapping of restraint 10 around the user without any neck or throat discomfort. The flexibility and padding of the foam material from which restraint 10 is constructed also aids in accomplishing this.

Figure 2:
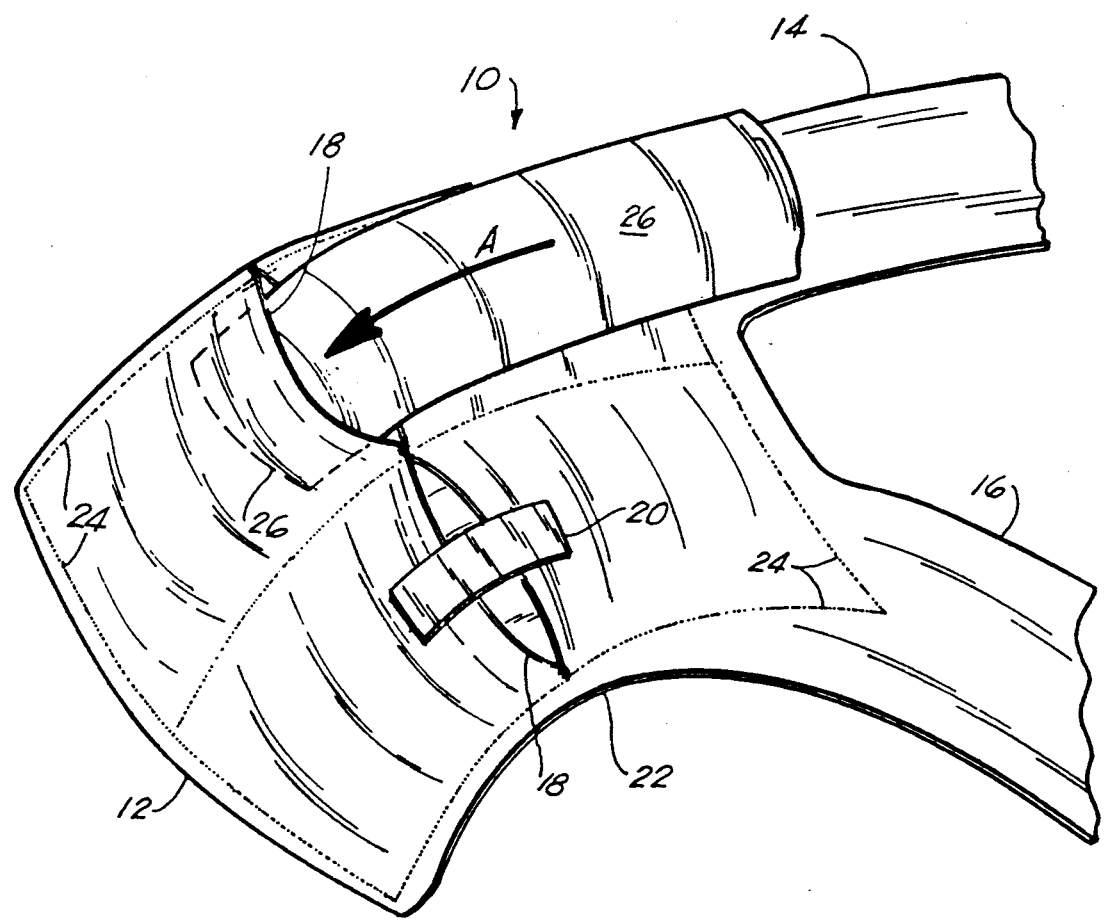
FIG. 2 is an enlarged view, partially broken away, of the embodiment of FIG. 1 illustrating the is insertion of either a hot or a cold pack.

Referring now to FIG. 2, there is shown an enlarged view of main body portion 12 with pockets 18. As illustrated, main body portion 12 is configured with four such pockets 18 although more or fewer pockets may be incorporated as needed. Stitching 24 outlines the dimensions of each such pocket 18 in this embodiment, but the additional material needed to create these pockets may be glued or otherwise bonded to main body portion 12 rather than being sewn. Pockets 18 are sized to accommodate or accept either hot or cold packs 26 therein as shown. Once packs 26 are inserted (ARROW "A"), they are retained in their respective pockets 18 via hook closure device 20. In this fashion, when packs 26 need to be replaced and/or recharged; they need merely be slipped out of their respective pockets 18 (opposite ARROW "A") without having to also remove or undo shoulder restraint 10.

Figure 3:
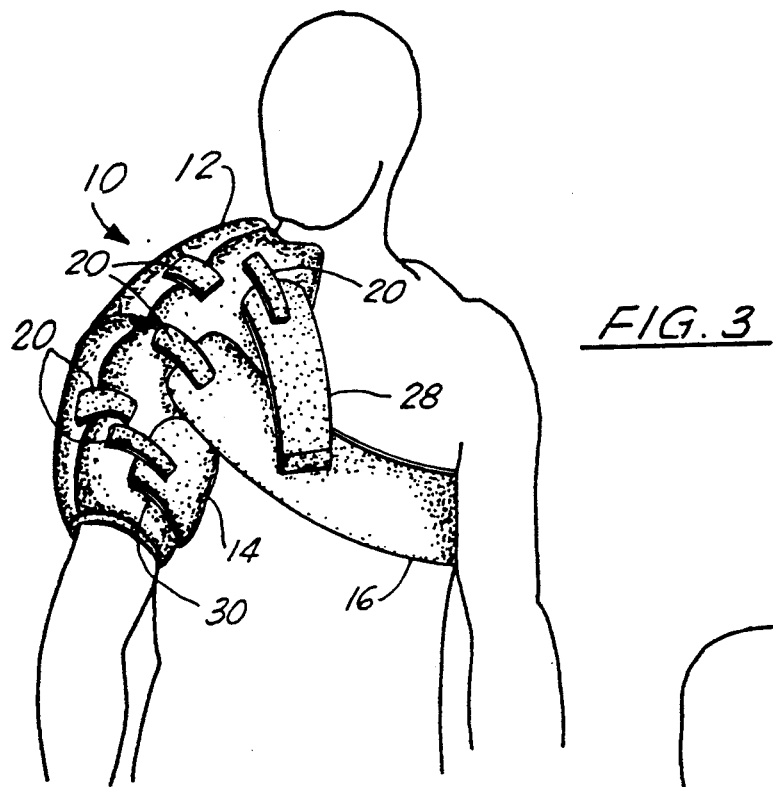
FIG. 3 is a front pictorial view of the embodiment of FIG. 1 as fitted to a user's shoulder illustrating the extra support strap in a frontal location; and, FIG. 4 is a back pictorial view of the embodiment of FIG. 1 as fitted to a user's shoulder illustrating the extra support strap in a back location.

Referring now to FIG. 3, the installation of shoulder harness 10 is shown with the addition of extra support strap 28. As illustrated, neck notch 22 is positioned against the user's neck (on either the user's right or left sides) with main body portion 12 being placed over the area of the body that is to be warmed or chilled by pack 26. Short first extension 14 is then wrapped around the user's upper arm with end region 30 being secured to main body portion 12 via hook closure device 20. (in some cases, should the user's arms be small in diameter, short extension 14 will be wrapped around itself thereby causing end 30 to be secured to an intermediate position of short extension 14.)

Prior, concurrent, or subsequent to the fastening of short extension 14, long extension 16 would be wrapped around the user's upper torso and secured in much the same way to main body portion 12 (or itself) via hook closure device 20. As shown, long extension 16 would be placed underneath the user's opposite arm so as not to interfere with its use while restraining the wrapped shoulder.

Figure 4:
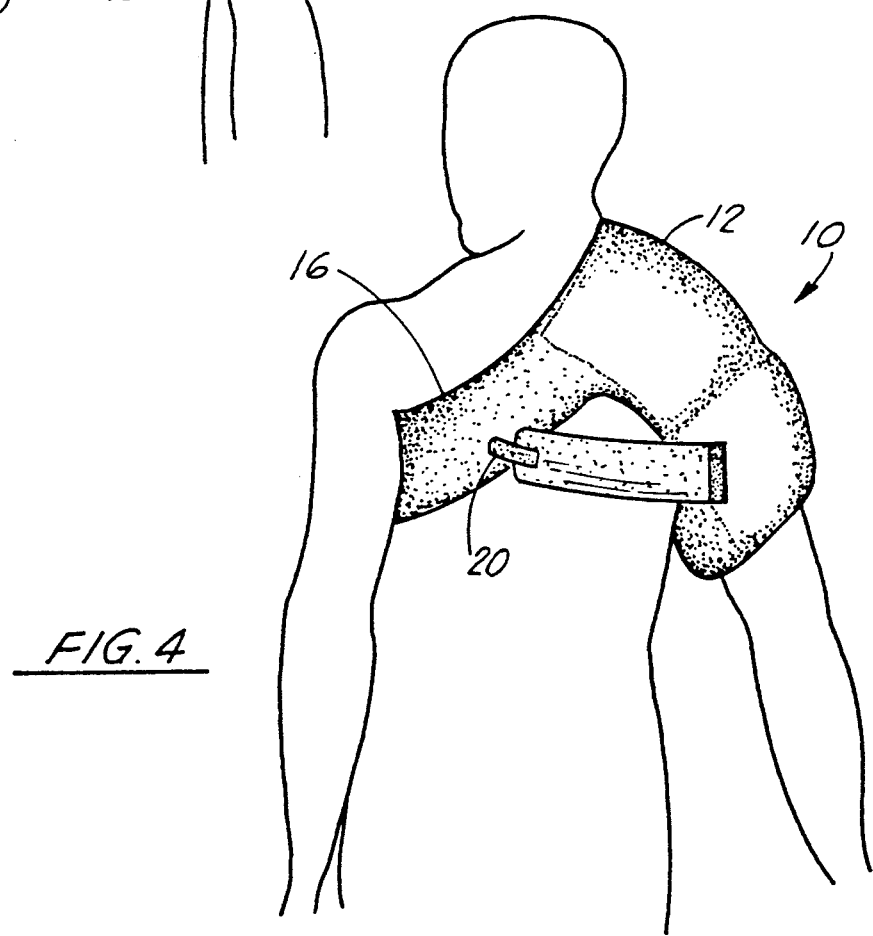

Should additional support be needed, extra support strap 28 can be fastened between main body portion 12 and long extension 16 in either a front position as shown in FIG. 3 or in a back position as shown in FIG. 4. This extra support strap 28 is fastened as above via hook closure device 20.

Once shoulder restraint 10 is installed, or prior to installation if so desired, a hot or cold pack 26 is inserted within one or more pockets 18 directly above the area to be heated or chilled. These packs 26 are secured within their respective pockets 18 via hook closure device 20. Later, should these packs 26 need to be replaced, the used one may be simply removed from its pocket 18 with a new one being inserted therein without the need to remove restraint 10.

While the embodiment disclosed herein has been described with respect to a shoulder region, this invention may also be easily adapted to other body parts as well. These other body parts including a torso area (front, back or side) as well as a hip or upper thigh region.

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

What is claimed as invention is:

1. A shoulder restraint comprising:
   (a) an one-piece main body portion for covering the shoulder area of the user, having a plurality of pockets therein, each of said pockets being sized and configured to accept a hot or cold pack therein, said main body portion being generally planar in configuration and having openings therein to permit insertion and removal of said packs;
   (b) a first extension extending linearly from one side of said main body portion, said first extension being of the same material as said main body portion;
   (c) a second extension, longer than said first extension, spaced apart from said first extension and extending linearly from the same said side of said main body portion, said second extension being of the same material as said main body portion;
   (d) detachable closure means for securing the ends of said first and second extensions to said main body portion; and,
   (e) detachable closure means for securing the closure of each of said pockets at said openings in said main body portion.

2. The apparatus of claim 1, wherein said shoulder restraint is covered with material comprising the loop of a hook and loop closure system and wherein said detachable closure means comprise the hook of said hook and loop closure system.

3. The apparatus of claim 2, wherein said second extension is curved and wherein said first extension may be curved or straight.

4. The apparatus of claim 3, wherein said main body portion is configured having a neck notch adjacent the base of said second extension.

5. The apparatus of claim 4, wherein said main body portion and both said extensions are of unitary and generally uniform construction.

6. The apparatus of claim 5, further comprising additional support means for supplying additional support between said main body portion and said second extension.

7. The apparatus of claim 6, wherein said main body portion comprises four said pockets, each being closable by said detachable closure means for securing the closure of said pockets.

8. A shoulder restraint comprising:
   (a) a main body portion for covering the shoulder area of the user, having a plurality of pockets therein, said pockets covering substantially the entire area of said main body portion, each of said pockets being sized and configured to accept a hot or cold pack therein, said main body portion being generally planar in configuration and having openings therein to permit insertion and removal of said packs;
   (b) a first extension extending linearly from one side of said main body portion, said first extension being of the same construction as said main body portion;
   (c) a second extension, longer than said first extension, spaced apart from said first extension and extending with an outward curvature from the same said side of said main body portion, said second extension being of the same construction as said main body portion;
   (d) detachable closure means for securing the ends of said first and second extensions to the side opposite said one side of said main body portion; and,
   (e) detachable closure means for securing the closure of each of said pockets at said openings in said main body portion.

9. A shoulder restraint comprising:
   (a) a main body portion for covering the shoulder area of the user, having a plurality of lateral pockets therein, said pockets covering substantially the entire area of said main body portion, each of said pockets being sized and configured to accept a hot or cold pack therein, said main body portion being generally planar in configuration and having transverse openings therein to permit insertion and removal of said packs;

(b) a first extension extending linearly from one side of said main body portion, said first extension being of the same construction as said main body portion;

(c) a second extension, longer than said first extension, spaced apart from said first extension and extending with an outward curvature from the same said side of said main body portion, said second extension being of the same construction as said main body portion;

(d) detachable closure means for securing the ends of said first and second extensions to the side opposite said one side of said main body portion; and, (e) detachable closure means for securing the closure of each of said pockets at said openings in said main body portion.

* * * * *